United States Patent
Shen et al.

(10) Patent No.: US 11,596,303 B1
(45) Date of Patent: Mar. 7, 2023

(54) IMAGING DEVICE

(71) Applicant: THE UNIVERSITY OF LIVERPOOL, Liverpool (GB)

(72) Inventors: Yaochun Shen, Liverpool (GB); Yalin Zheng, Liverpool (GB); Samuel Lawman, Liverpool (GB); Xiaoran Li, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 0 days.

(21) Appl. No.: 17/799,633

(22) PCT Filed: Feb. 12, 2021

(86) PCT No.: PCT/GB2021/050339
§ 371 (c)(1),
(2) Date: Aug. 12, 2022

(87) PCT Pub. No.: WO2021/161030
PCT Pub. Date: Aug. 19, 2021

(30) Foreign Application Priority Data

Feb. 13, 2020 (GB) ..................... 2002009

(51) Int. Cl.
*A61B 3/18* (2006.01)
*A61B 3/00* (2006.01)
(Continued)

(52) U.S. Cl.
CPC .............. *A61B 3/18* (2013.01); *A61B 3/0008* (2013.01); *A61B 3/102* (2013.01); *A61B 3/14* (2013.01)

(58) Field of Classification Search
CPC ......... A61B 3/18; A61B 3/0008; A61B 3/102; A61B 3/14
(Continued)

(56) References Cited

U.S. PATENT DOCUMENTS

2007/0291277 A1* 12/2007 Everett .............. G01B 9/02077
356/497
2010/0182612 A1 7/2010 Hirofumi et al.
(Continued)

FOREIGN PATENT DOCUMENTS

| EP | 3081146 A1 | 10/2016 |
| WO | WO 2012130818 A1 | 10/2012 |
| WO | WO 2013097885 A1 | 7/2013 |

OTHER PUBLICATIONS

PCT/GB2021/050339 International Search Report and Written Opinion dated May 26, 2021, 13 pages.
(Continued)

*Primary Examiner* — Mohammed A Hasan
(74) *Attorney, Agent, or Firm* — Lathrop GPM LLP

(57) ABSTRACT

There is provided an imaging device (100) for imaging a target, the imaging device (100) comprising a Scheimpflug imaging system (102) and an Optical Coherence Tomography, OCT, imaging system (104), where the Scheimpflug imaging system (102) comprises a camera (112) and a lens system (108), and the OCT imaging system (104) comprises an imaging optical element and a detector (122). The imaging device (100) further comprises a light source (106) adapted to provide a light beam suitable for operation of the Scheimpflug imaging system (102) and the OCT imaging system (104). The lens system (108) of the Scheimpflug imaging (102) system is configured to provide an adjustable focal length.

18 Claims, 17 Drawing Sheets

(51) Int. Cl.
*A61B 3/14* (2006.01)
*A61B 3/10* (2006.01)

(58) Field of Classification Search
USPC ........................................................ 351/206
See application file for complete search history.

(56) References Cited

U.S. PATENT DOCUMENTS

| | | |
|---|---|---|
| 2013/0085370 A1 | 4/2013 | Freidman et al. |
| 2013/0103014 A1* | 4/2013 | Gooding ............. A61B 3/0025 606/4 |
| 2014/0049748 A1 | 2/2014 | Hee |
| 2017/0007112 A1* | 1/2017 | Gonzalez ............. A61B 3/0025 |
| 2018/0289260 A1 | 10/2018 | Matsunobu et al. |

OTHER PUBLICATIONS

GB Patent Application No. 2002009.5 Search Report dated Aug. 18, 2020, 2 pages.

* cited by examiner

IMAGING DEVICE

This invention relates to an imaging device. In particular, it relates to an imaging device for imaging a target, such as an eye. The imaging device comprises a Scheimpflug imaging system and an Optical Coherence Tomography (OCT) imaging system.

BACKGROUND

Cross sectional imaging is a key tool in the assessment and diagnosis of diseases and conditions affecting the anterior segment structures in the eye. In conventional clinical practice, imaging of the anterior segment has traditionally been carried out with slit lamp biomicroscopy. For objective quantitative assessment of anterior segment structures, anterior segment imaging modalities such as Optical Coherence Tomography (OCT) dedicated for anterior segment and rotating Scheimpflug imaging have become established in recent decades. They provide quantitative information and qualitative imaging of the cornea, anterior chamber, iris, iridocorneal angle and lens. In the current practice, Scheimpflug imaging and OCT imaging are essentially two different devices that provide complementary information of the eye. Consequently, patients have to undergo two examinations in order to give clinicians clinical information for their management of eye disease. This costs money and time to both patients and the healthcare provider.

In addition, Scheimpflug imaging can image the anterior segment with almost the whole width and with high imaging depth (~10 mm), but it cannot simultaneously provide sufficient high resolution for imaging the fine cellular layers of the cornea and the tear film, and it cannot be used for retina imaging. Whereas, an OCT system can be designed to image the cornea and retina at a higher axial resolution but at limited image depth (~2 mm).

BRIEF SUMMARY OF THE DISCLOSURE

In accordance with an aspect of the present disclosure there is provided an imaging device for imaging a target. The imaging device comprises a Scheimpflug imaging system and an Optical Coherence Tomography (OCT) imaging system, where the Scheimpflug imaging system comprises a camera and a lens system, and the OCT imaging system comprises an imaging optical element and a detector. The imaging device further comprises a light source adapted to provide illumination suitable for operation of the Scheimpflug imaging system and the OCT imaging system. The Scheimpflug imaging system is configured to maintain the camera at the image plane of the lens system without moving the Scheimpflug imaging system. The camera may be maintained at the image plane of the lens system by the lens system having an adjustable focal length.

In accordance with another aspect of the present disclosure there is provided a dual imaging device. In particular, it relates to a dual 3D imaging device for imaging a target, such as an eye. The imaging device comprises a combined raster scanned Optical Coherence Tomography (OCT) imaging system, and a simultaneous Scheimpflug imaging system, which maintains a high imaging resolution over the whole volume.

Embodiments of the invention are defined in the appended claims.

BRIEF DESCRIPTION OF THE DRAWINGS

Embodiments of the invention are further described hereinafter with reference to the accompanying drawings, in which.

DETAILED DESCRIPTION

Figure 1A:
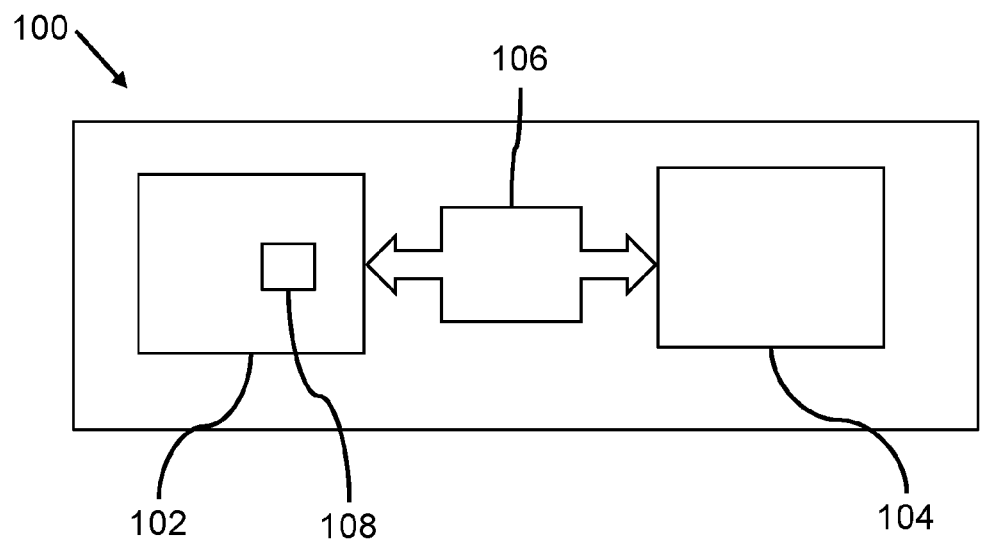
FIG. 1(a) is a block diagram of an imaging device according to the disclosure.

Referring to FIG. 1(a), there is shown a block diagram of an imaging device for imaging a target, such as an eye, according to an aspect of the disclosure. The imaging device, indicated generally by the reference numeral 100, comprises a Scheimpflug Imaging (SI) system 102 and an Optical Coherence Tomography (OCT) imaging system 104. The imaging device further comprises a light source 106, which provides a light beam for the Scheimpflug imaging system 102 and the OCT imaging system 104. The light source 106 may comprise a shared light source that provides a suitable light beam for both imaging systems simultaneously. In this way, each photon from the light source 106 acts as an illuminating photon for the OCT imaging system 104 while at the same time acting as an illuminating photon for the SI system 102. Alternatively, the light source may comprise a separate light source for each of the SI system 102 and OCT imaging system 104. The Scheimpflug imaging system 102 is configured to provide an adjustable focal length. This may be provided by a lens system 108 adapted to provide a variation in focal length, however, alternative arrangements, such as a movable camera, may be implemented. By having an SI system with an adjustable focal length, the imaging device 100 may perform Scheimpflug imaging and OCT imaging simultaneously, without rotation of the Scheimpflug imaging system 102.

Figure 1B:
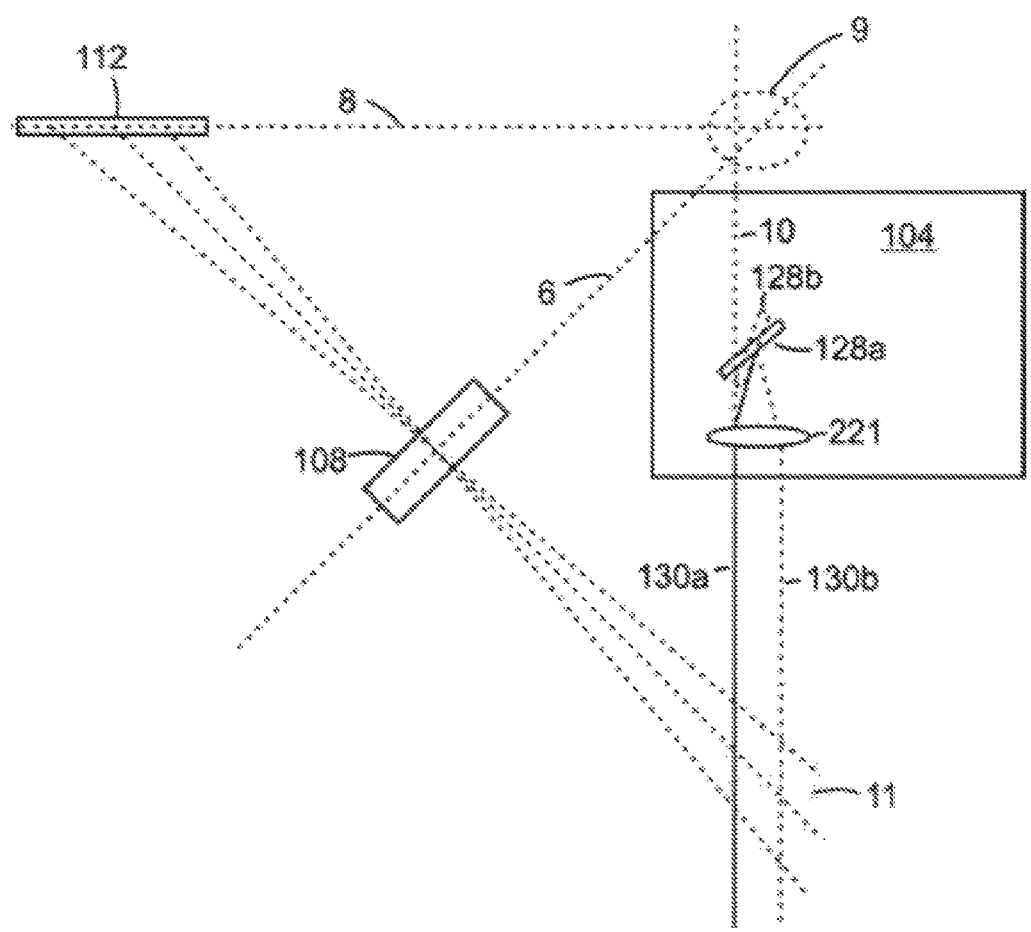
FIG. 1(b) is a schematic diagram of an imaging device according to the disclosure.

Referring to FIG. 1(b), there is shown a schematic representation of an example of the imaging device of the disclosure. The imaging device 100 comprises an OCT imaging system 104, of scanning point or line-field format, and a Scheimpflug imaging system. The OCT imaging system 104 is setup to image a target 11. The OCT imaging system 104 comprises a beam scanning mechanism 128 for moving the light beam over the target to be imaged. The beam may be moved over the target in one or two dimensions. The beam scanning mechanism 128 may comprise one or more scanning mirrors. The OCT imaging system 104 further comprises a beam imaging mechanism to create appropriate focus of a scanning point or line field onto the target 11. The beam imaging mechanism may be understood to refer to an objective lens 221. In the example implementation shown in FIG. 1(b), the OCT objective lens 221 is placed in the common telecentric arrangement widely used in OCT and other point and line-field scanned optical methods. The telecentric arrangement allows the scanned beam, 130a and 130b, to be in parallel to the optical axis so that the measured image data is not distorted in Cartesian coordinates. Two temporal locations of the beam scanning mechanism 128 are shown, a first location 128a and a second location 128b, showing how the beam is scanned over the target 11 to reconstruct 3D (and 2D in scanning point systems) images. At the time of first location 128a, the axial path of the illuminating beam is shown as a first path 130a, from which an illumination plane 10 is defined. At the time of the second location 128b, the axial path of the illuminating beam is shown as a second path 130b. Thus, the illumination plane 10 moves as the light beam is scanned.

The Scheimpflug imaging system comprises a lens system 108 with principal plane 6, and a two-dimensional camera 112, having an image plane 8. The Scheimpflug imaging system is adapted to take a Scheimpflug image volume of the target 11 using the light beam used by the OCT imaging system 104. Advantageously, the camera 112 may be a CCD or CMOS camera, or other suitable camera. The image plane 8 may be referred to as a detection plane 8. The lens system 108 may comprise a single lens, or a lens system comprising a combination of two or more lenses. A separate light source may be used instead of that used by the OCT imaging system 104. The Scheimpflug imaging system is configured such that the focal length is automatically adjustable, for example the lens assembly 108 may comprise a lens having an automatically adjustable focal length. Alternatively the camera position could be automatically adjusted to match the image plane of the Scheimpflug imaging system. The focal length of the lens system or camera position is adjusted in synchronicity with the movement of the beam scanning mechanism. This adjustable focal length arrangement allows taking the Scheimpflug image volume without blurring due to defocus through the volume. In the majority of cases and times, the image plane 8 and the principal plane 6 will converge approximately in the volume 9, giving the majority of, but not perfect, benefits of the Scheimpflug principle. Designs that do achieve perfect (within engineering tolerances) Scheimpflug correction are disclosed herein, but should be regarded as example for ease of description. For the majority of realisations, in particular the telecentric case, the imaging will be carried out in an approximation of perfect Scheimpflug principles.

Figure 2A:
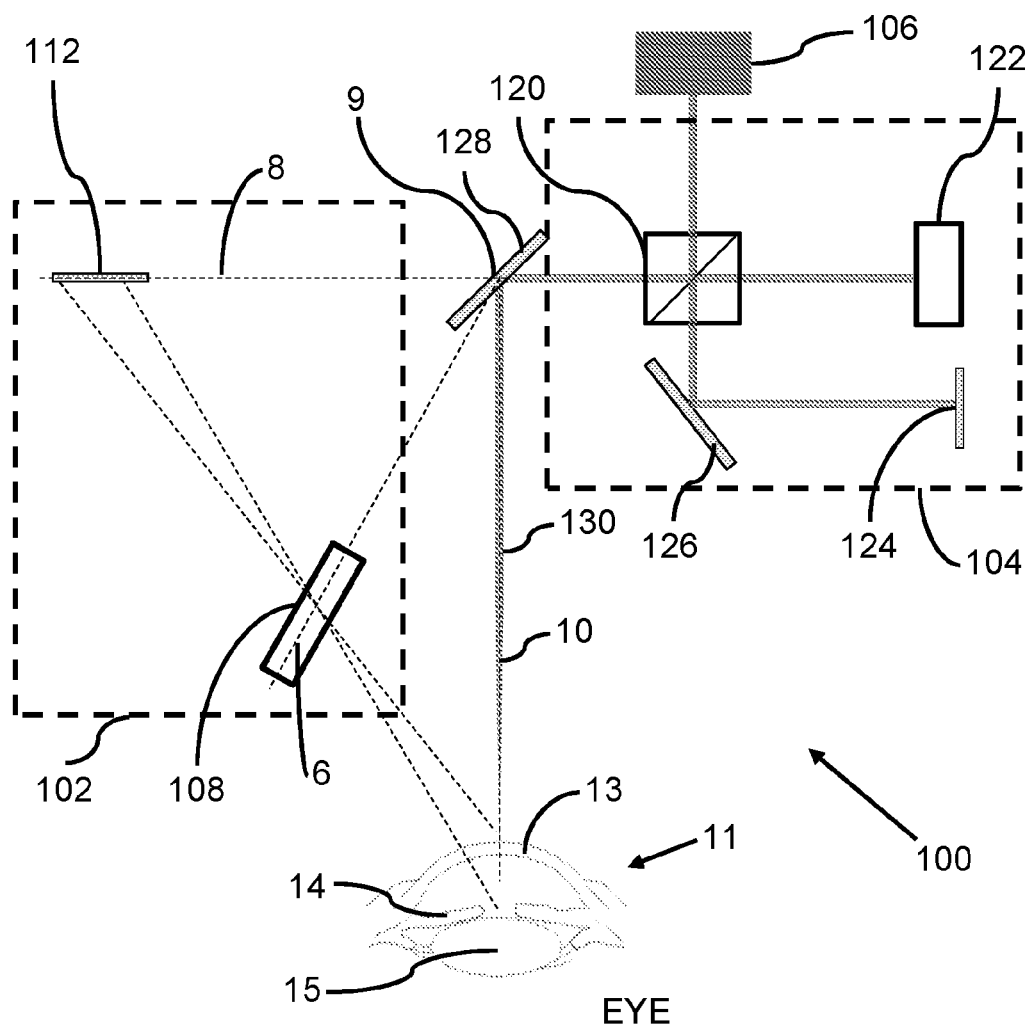
FIG. 2(a) is a schematic diagram of an example according to the disclosure using spectral domain Optical Coherence Tomography (SD-OCT), in the case of perfect Scheimpflug arrangement.
Figure 2B:
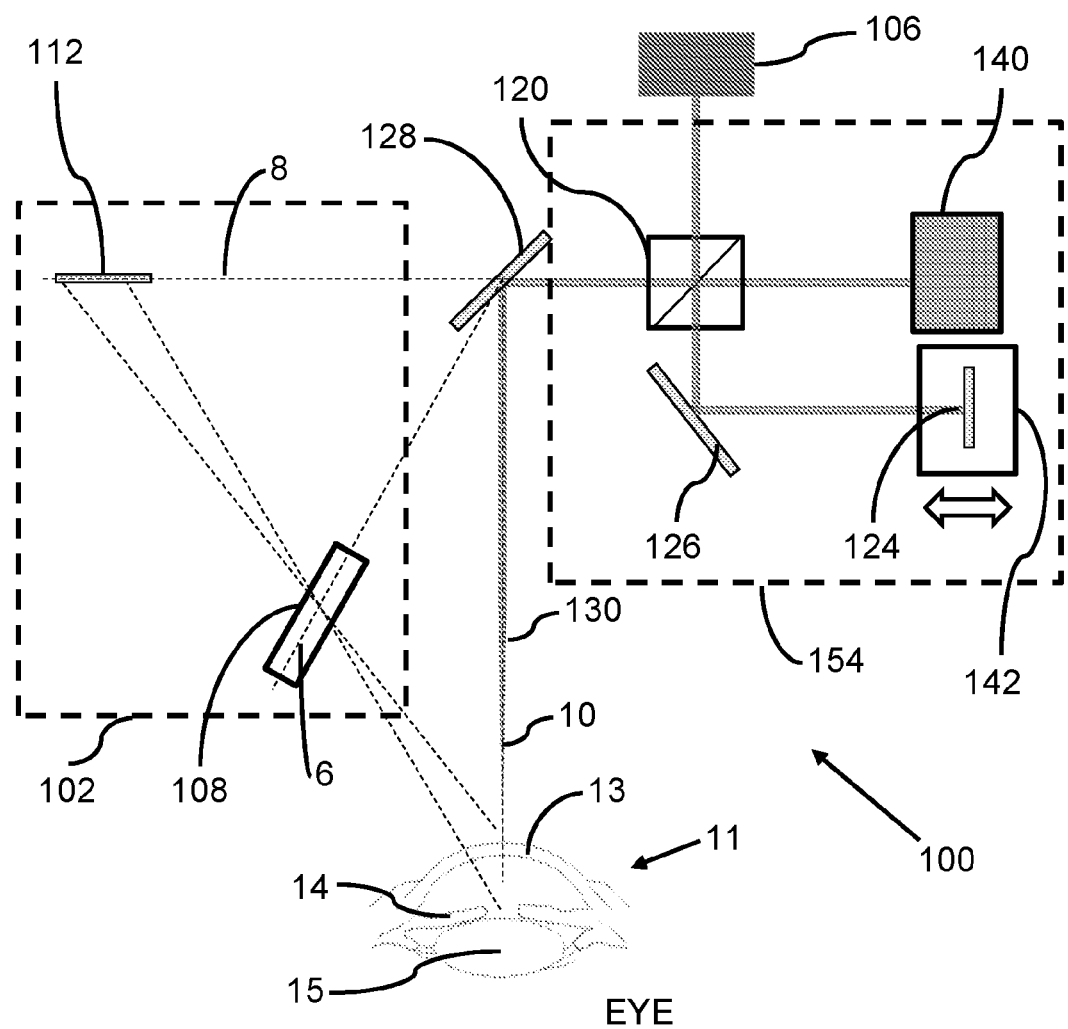
FIG. 2(b) is a schematic diagram of an example according to the disclosure using time domain Optical Coherence Tomography (TD-OCT), in the case of perfect Scheimpflug arrangement.
Figure 2C:
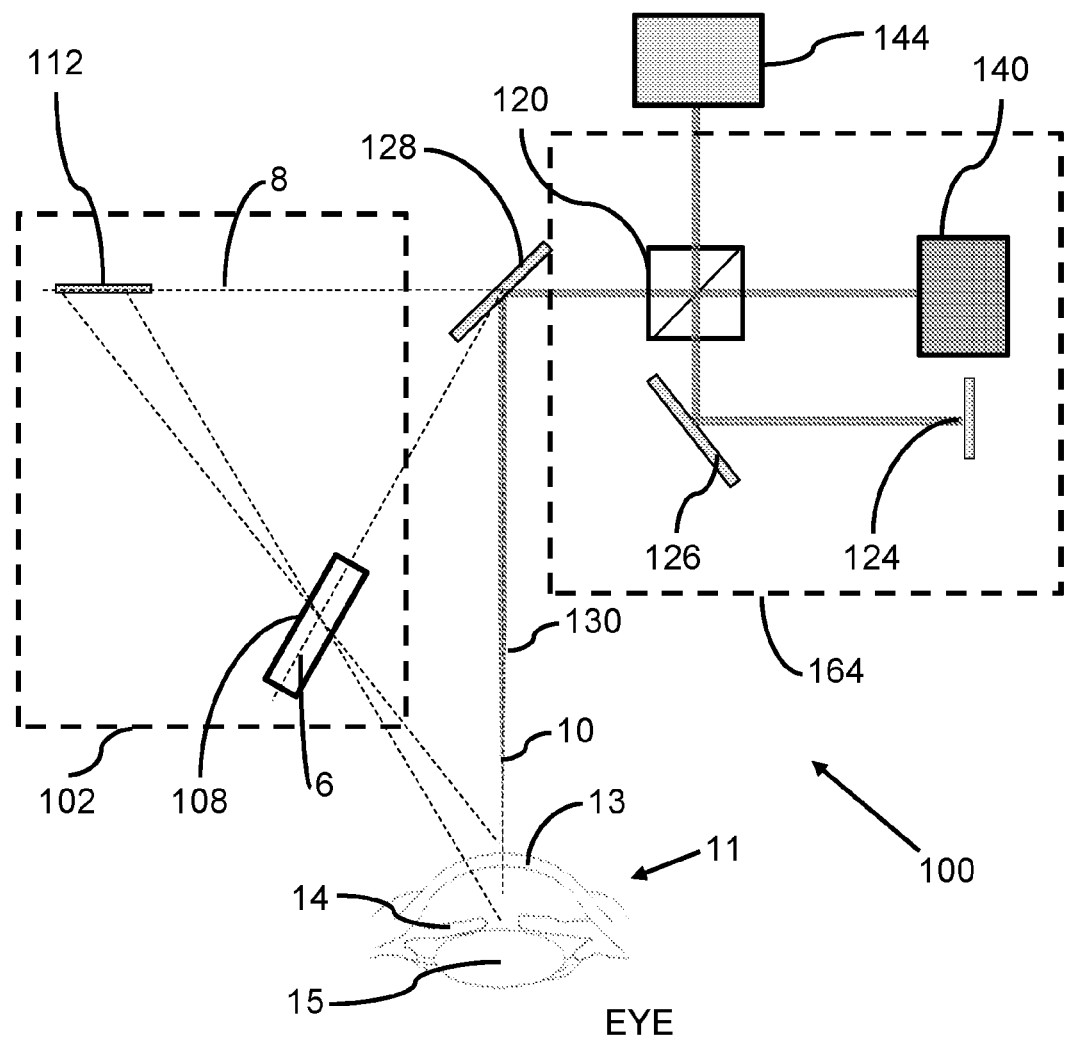
FIG. 2(c) is a schematic diagram of an example according to the disclosure using swept source Optical Coherence Tomography (SS-OCT), in the case of perfect Scheimpflug arrangement.
Figure 2D:
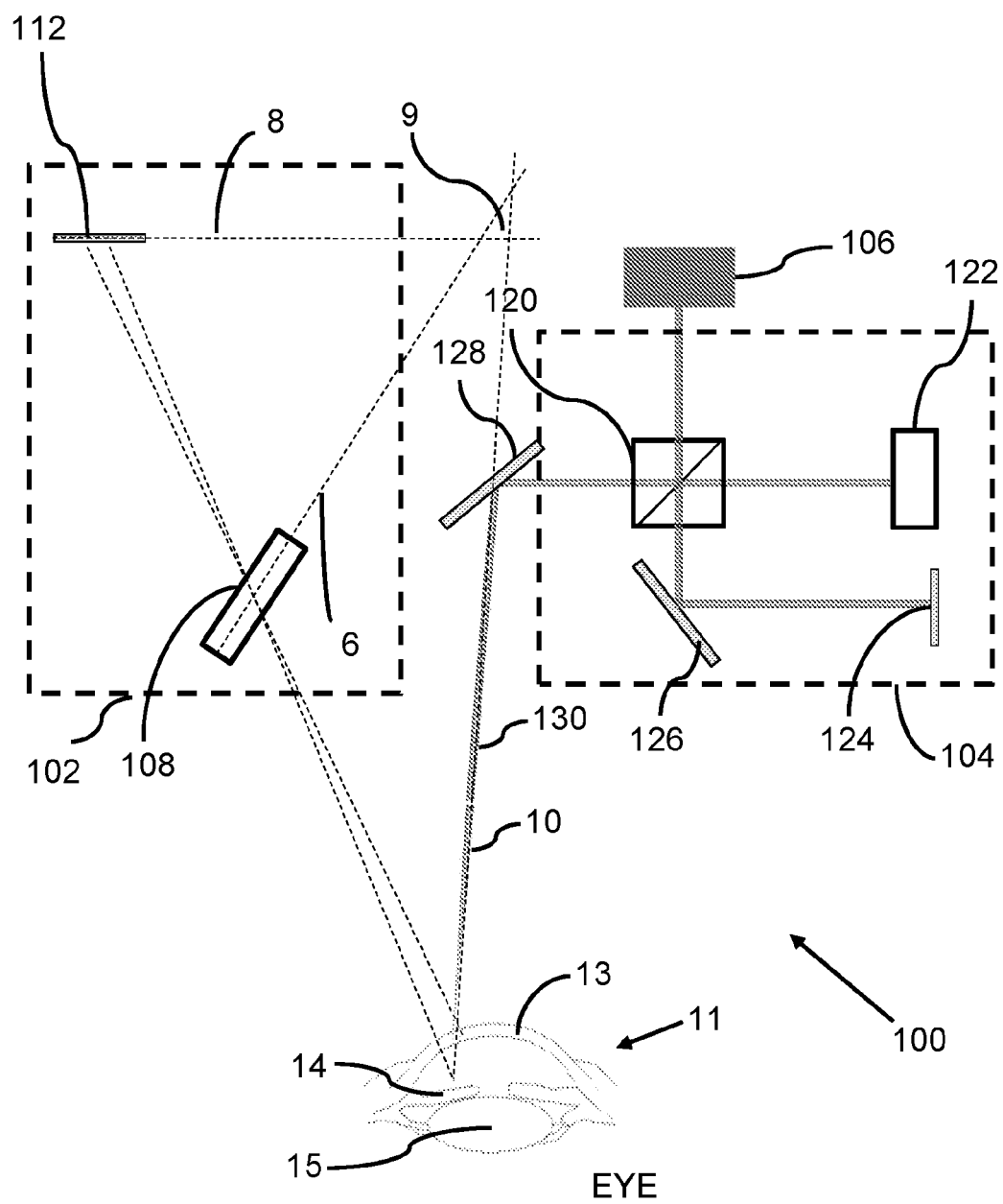
FIG. 2(d) is a schematic diagram of an example where imperfect Scheimpflug illumination is used.

Referring to FIG. 2(a), there is shown a schematic illustration of an example of the imaging device 100. The imaging device 100 is shown in the process of imaging a target, in this case an eye, indicated generally by the reference numeral 11. The eye 11 is shown to comprise the cornea 13, iris 14 and lens 15. The Scheimpflug imaging system 102 comprises a camera 112, having an image plane 8; and a lens system 108, having a principal plane 6. The camera 112 may be any detector or camera suitable for use in a known Scheimpflug imaging system, or other suitable detector. The lens system 108 has an adjustable focal length. The focal length may be electrically adjustable. The focal length may be adjustable in response to a control signal. The principal plane 6 and the image plane 8 intersect at a scanning mirror 128. The scanning mirror 128 is an example of a beam scanning mechanism 128, as discussed in relation to FIG. 1(b), and may also be referred to as a galvanometer scanner. The scanning mirror 128 directs the incident light beam 130 at the target 11. The area of intersection 9 between the image plane 8, principal plane 6 and sample plane 10 may be referred to as the Scheimpflug Intersection 9. The Scheimpflug Intersection 9 is a single point or line in a perfectly arranged Scheimpflug imaging system, however, in non-perfect arrangements the actual intersection may be a volume surrounding that ideal location. Where the Scheimpflug Intersection 9 is a line, it may be understood to be extending perpendicular to the figure.

Figure 3:
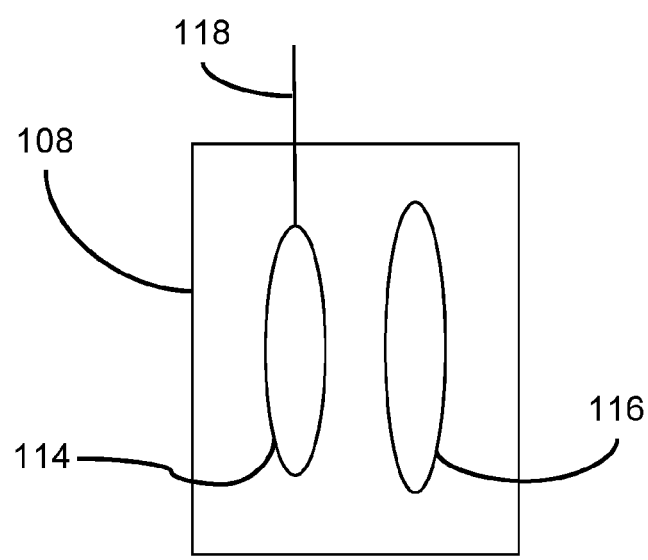
FIG. 3 is a diagrammatic representation of a lens system suitable for use in the Scheimpflug imaging system of the disclosure.

Referring to FIG. 3, there is shown a diagrammatic representation of a lens system 108 suitable for use in the imaging device 100. The lens system 108 comprises a lens 114 having an adjustable focal length. Such a lens may also be referred to as a focus-tuneable lens. The lens 114 receives a control signal via an input 118 which controls the focal length of the lens 114. In an example, the focal length of the lens 114 is adjustable in response to the electrical current or voltage supplied to the lens 114. A suitable lens is available from Edmund Optics, model number EL-10-30-Ci-NIR-LD, <https://www.edmundoptics.com/p/5-to-10-diopters-nir-op-totune-industrial-focus-tunable-lens/31418/>. This device has a focus range of +5 to +10 diopter (a focal length of 100 mm to 200 mm). The lens system may comprise an additional lens 116 so that the lens system 108 has the desired focus power. As such, the lens system 108 has an electrically-adjustable focal length such that the combined lens power will allow a clear image of the eye to be formed at the image plane 8 of the camera 112. The additional lens may have a focal length of 100 mm, such that the focal length of the lens system 108 has an overall variable focal length of 50 mm to 66.7 mm. In an example, the focal length of the lens system 108 may vary by ±6 mm.

Referring again to FIG. 2(*a*), the imaging device 100 further comprises the OCT imaging system 104, which in turn comprises a beam splitter 120, a spectrometer 122 acting as a detector, a reference object 124, such as a plate. A beam of light is directed towards the reference object by a mirror 126. The imaging device 100 is shown using spectral domain OCT (SD-OCT), but the invention is not limited thereto. The imaging device 100 further comprises the light source 106, which is a shared light source, and the scanning mirror 128, which is positioned to direct light received from the shared light source 106 via the beam splitter towards the eye 11. The scanning mirror 128 may be controlled in synchronicity with the adjustments to the Scheimpflug imaging system that allow the image plane thereof to be located at the camera 112. The shared light source may provide light in the visible or near infra-red region. The incident beam 130 directed at the target 11 by the OCT system 104 defines a sample plane 10. The principal plane 6 of the lens system 108 intersects the image plane 8 of the Scheimpflug imaging system 102 and the sample plane 10 (shown as a dashed line within the beam 130) at the surface of the scanning mirror 128. In this way, a clear image of the sample plane is always formed at the image plane 8 of the camera 112 of the Scheimpflug imaging system 102 or within its imaging depth range.

The path of the visible or near-infrared incident beam 130 incidents into the eye 11. The beam 130 enters the anterior segment of the eye 11, which contains the cornea 13, iris 14 and lens 15. Due to light scattering, a cross sectional image can be recorded by the camera 112 of the SI system 102. Due to back light scattering a separate cross-sectional image can be recorded by the OCT system 104.

Referring to FIG. 2(*b*), there is shown a schematic illustration of the imaging device 100 similar to that shown in FIG. 2(*a*), except that in FIG. 2(*b*) the OCT imaging system 154 of the imaging device 100 uses time domain OCT (TD-OCT). As such, the spectrometer 122 is replaced by a photodetector 140, and the reference object 124 is located on a moveable stage 142. The TD-OCT may be used either in a single-point or line-field configuration.

Referring to FIG. 2(*c*), there is shown a schematic illustration of the imaging device 100 similar to that shown in FIGS. 2(*a*) and 2(*b*), except that in FIG. 2(*c*) the OCT imaging system 164 of the imaging device uses swept source OCT (TD-OCT). As such, the OCT system 164 comprises a photodetector 140, and the light source is a tuneable swept laser 144.

Referring to FIG. 2(*d*), there is shown a schematic illustration of the imaging device 100 similar to that shown in FIG. 2(*a*), showing an example of imperfect Scheimpflug illumination. In this example, the illumination plane 10, image plane 8 and principal plane 6 of the lens system do not intersect at a single point. In this way, the Scheimpflug intersection is a volume. The imaging devices of the disclosure will provide useful imaging results even in the case of imperfect Scheimpflug illumination.

Figure 4A:
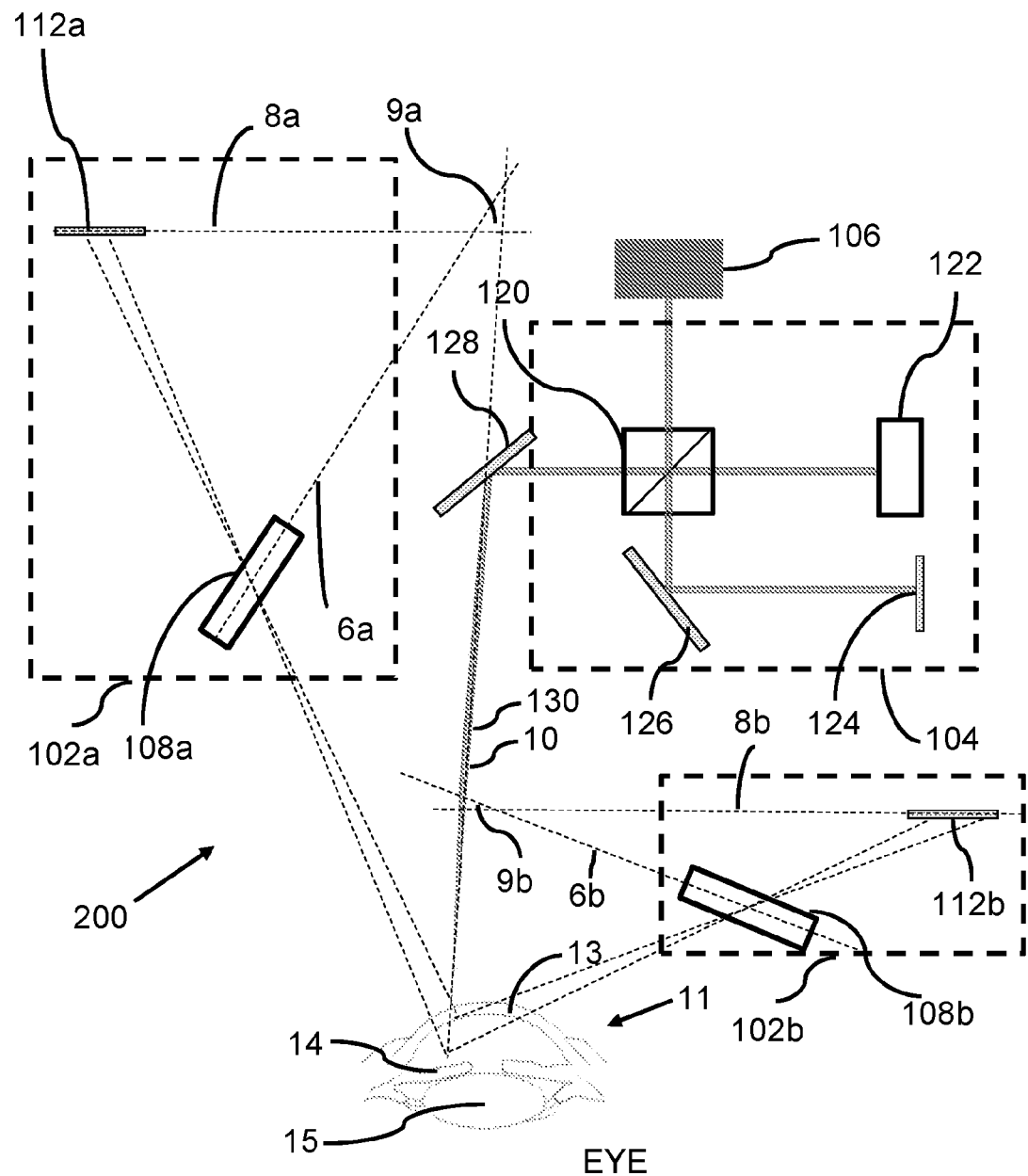
FIG. 4(a) is a schematic diagram of an example using two or more Scheimpflug imaging systems.
Figure 4B:
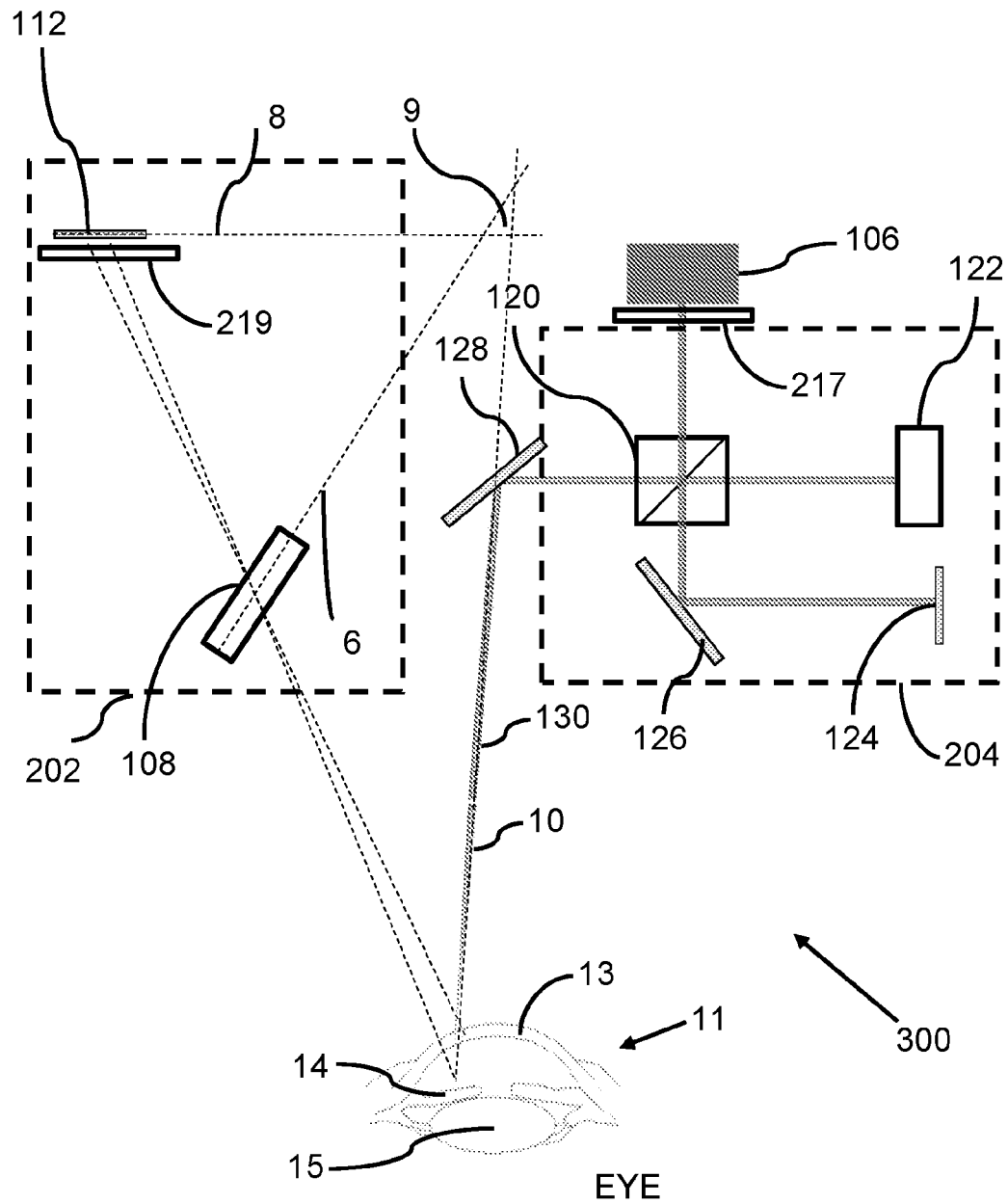
FIG. 4(b) is a schematic diagram of an imaging device according to the disclosure including polarising components.

Referring to FIG. 4(*a*), there is shown a schematic illustration of an imaging device according to the disclosure, indicated by the reference numeral 200. This example comprises a pair of the Scheimpflug Imaging systems of previous examples, and an OCT imaging system. The imaging device 200 may comprises a first Scheimpflug imaging system 102*a*, a second Scheimpflug imaging system 102*b*, and an OCT imaging system 104 similar to that shown in FIG. 2(*a*). Each of the first Scheimpflug imaging system 102*a* and the second Scheimpflug imaging system 102*b* are configured to provide an adjustable focal length, for example via the use of a lens system having an electronically-adjustable focal length. The imaging device 200 is shown using spectral domain OCT (SD-OCT), but the invention is not limited thereto. Using common path linefield OCT would be also be useful as it does not require a separate reference beam, making it more compact and thus easier to be integrated with the two (or more) Scheimpflug imaging devices 402.

The first Scheimpflug imaging system 102*a* comprises a first camera 112*a* having a first image plane 8*a*, and a first lens system 108*a* having an adjustable focal length. The second Scheimpflug imaging system 102*b* comprises a second camera 112*b* having a second image plane 8*b*, and a second lens system 108*b* having an adjustable focal length. For the double SI device, the cameras 112*a*, 112*b* and lens systems 108*a*, 108*b* are placed according to the Scheimpflug principle. In the illustrated examples, the SI systems 102*a*, 102*b* are shown using imperfect Scheimpflug illumination. Both SI systems start to image when the incident light scans the target eye 11. Therefore, for each scanning position of the light on the target 11, two SI images and one OCT image are taken simultaneously. Since all three images originate from the same illuminated part of a sample using a single light source, they provide cross-validation or cross-compensation mechanisms, leading to better image and understanding of the sample under study. The use of a single light source illumination for both OCT and SI systems simplifies the overall device structure as only one set of light delivery and scanning optics is necessary. The invention also enables the SI system to be made as an add-on module that can be added to existing OCT system which already has its light source and beam scanning optics. In this case, the sample is illuminated by the OCT light source only since there is no extra active light source used in the SI module. SI module acts like a passive imaging device and this simplifies the laser safety requirement. One still needs to synchronise the SI image acquisition with the movement of the optical scanner.

Referring to FIG. 4(*b*), there is shown a schematic illustration of an alternative example of imaging device according to the disclosure, indicated generally by the reference numeral 300. The imaging device 300 shown in FIG. 4(*b*) is similar to that shown in FIG. 2(*a*), and the same reference numerals are the used where appropriate. The imaging device 300 of FIG. 4(*b*) is adapted to overcome artefacts arising from specular reflected light in the Scheimpflug image, by using polarising components.

The imaging device 300 shown in FIG. 4(*b*) comprises a Scheimpflug imaging system 202 and an OCT imaging system 204. The Scheimpflug imaging system 202 is comprised of a camera 112 and a lens system 108, the lens system 108 having an adjustable lens (not shown) and an additional lens (not shown) to provide the desired combined focus power. The lens system 108 has a principal plane 6. The focal length of the adjustable lens 114 is controlled by the electrical current/voltage supplied to the adjustable lens 114. Thus, the focal length of the combined optical element 108 can be electrically changed.

According to the Scheimpflug principle and similar to the operation of the imaging device 100 of FIG. 2(a), the principal plane 6 of the lens system 108 and the illumination plane 10 ideally intersect the image plane 8 at a point 9, however in the case of imperfect Scheimpflug illumination, the intersection 9 is a volume. The incident beam 130 travels along the illumination plane and incidents into the eye 11. The SI system 202 captures an image from angular light scattering, and a separate cross-sectional image can be recorded by the OCT system 204 due to back light scattering.

Figure 9:
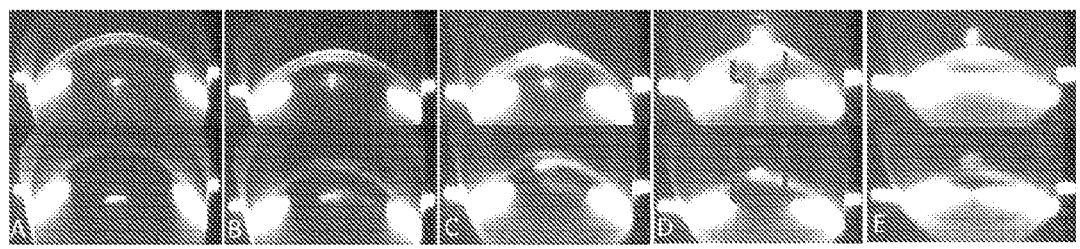
FIG. 9 is a set of Scheimpflug images of a porcine eye in 3D scans using an imaging device of the disclosure with and without polarizers.

In practise, not only scattered light, but also specular reflected light from surfaces can be recorded by the camera. This reflected light may cause saturation to the detectors thus leading to a strong artefact at certain positions. In order to avoid this reflection artefact, a first polariser 217 is placed in the path of the incident beam 130. The first polarizer 217 is shown adjacent to the light source 106, but it will be understood that the first polarizer 217 can be positioned anywhere in the beam path before the sample. Alternatively a polarised light source may be used. A second polariser 219 is placed in front of the camera 112. The second polarizer 219 can be positioned anywhere in the beam after the sample. The reflected light will preserve the polarisation of the incident light whilst the scattered light may change its polarisation. By carefully choosing the relative polarisation direction of these two polarisers, the reflection light can be reduced/blocked and only scattering light is recorded by the camera 112. The effect of the polarizer on the Scheimpflug system is shown in FIG. 9.

Figure 5:
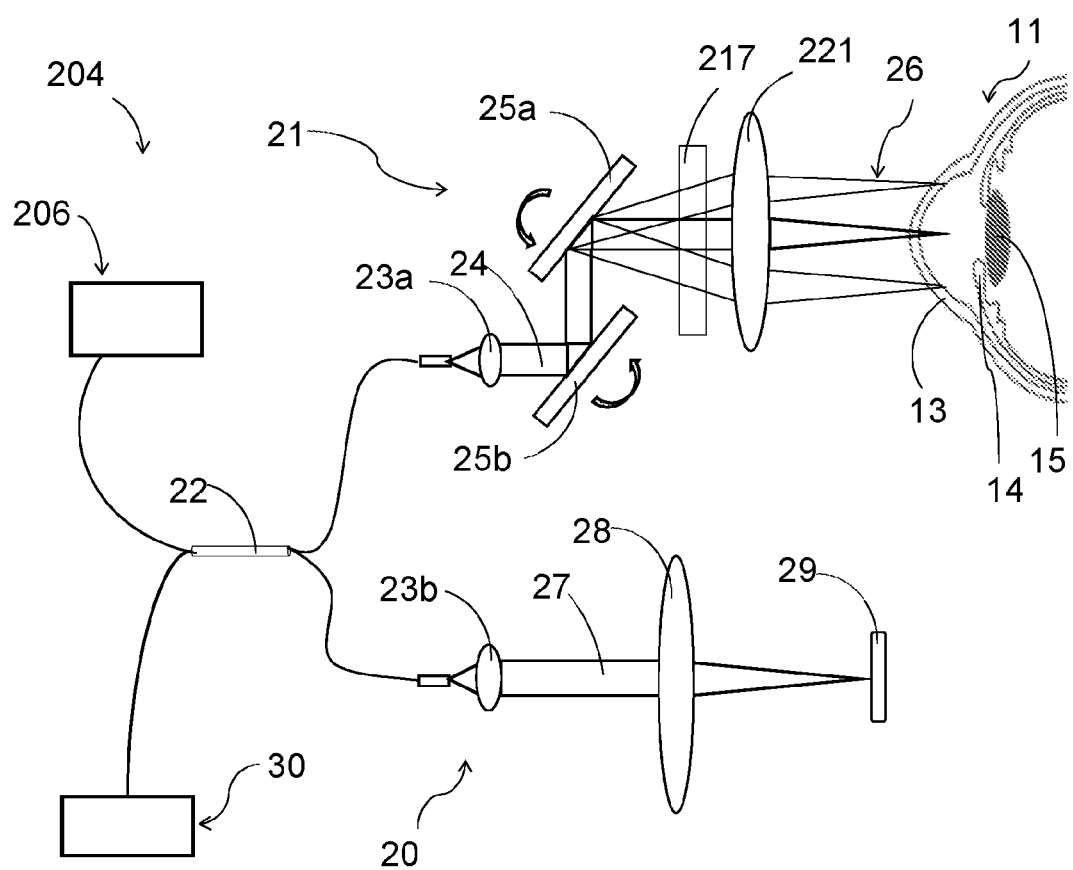
FIG. 5 is a schematic illustration of a prior art Optical Coherence Tomography (OCT) imaging system under scanning point configuration.

An example of an OCT imaging system 204 that is suitable for use in the imaging devices of the disclosure is shown in greater detail in FIG. 5, however the person skilled in the art will understand that other arrangements of OCT, including those described in relation to FIGS. 2(a), 2(b), 2(c) and 2(d) may also be used. The light from the broadband light source 206 is split into a reference arm 20 and a sample arm 21 by a fibre coupler 22. A collimator 23a in the sample arm 21 transforms the point light into a parallel beam 24 of collimated light. A collimator 23b in the sample arm 20 transforms the point light into a parallel beam 27 of collimated light. On the sample arm 21, the collimated beam 24 after collimator 23a illuminates a beam scanning mechanism in the form of a 2D galvanometer scanner 25a. The 2D galvanometer scanner 25 (for example, Thorlabs, GVS002) is used to move the incident beam to form a line. This may be referred to as scanning the beam. The objective lens 221 focuses the beam 26 onto a target. In the reference arm 20, the collimated light 27 is focused by an objective lens 28 and incident to a piece of glass 29. The light reflected back from the reference arm 20 and the scattered light from sample arm 21 is collected and measured using a detector, in this case a spectrometer 30. The OCT system 204 may comprise a controller (not shown) to control the movement of the beam by the galvanometer scanner 25, and may control other components as required.

Considering FIG. 5 in combination with the imaging devices shown in FIGS. 2(a), 2(b), 2(c) and 2(d), the light beam emitted from the first collimator 23a in FIG. 5 is incident on the mirror surface of the galvanometer scanner 25, which is understood to be equivalent to the scanning mirror 128 at point 9, where the principal plane 6 of the lens system 108 intersects the image plane 8 of the camera 112.

In use, the imaging devices of the disclosure use the scanning mirror 128 or equivalent to move the incident beam 130 during the examination of the target. A B-scan can be obtained when the scanning mirror 128 rotates along the vertical direction (perpendicular to the page). Each B-scan map comprises a number of A-scans and each A-scan waveform provides depth profile information of the sample along the scanned path of the incident beam 130. With the scanning mirror 128 scanning the incident beam, the camera 112 and the OCT system 104 records a Scheimpflug image and an OCT image of the same illuminated sample cross-sectional area of the eye 11 simultaneously. Multiple B-scans can be obtained when the scanning mirror 128 rotates along vertical and horizontal directions sequentially to carry out a 3D scan. For the Scheimpflug imaging system 102, an arrangement adapted to provide an adjustable focal length, such as an electronically-adjustable lens 114 providing a lens assembly with an adjustable focal length, allows a clear image of the illuminated portion of the sample to be formed at the image plane 8 throughout the OCT imaging process.

Figure 10:
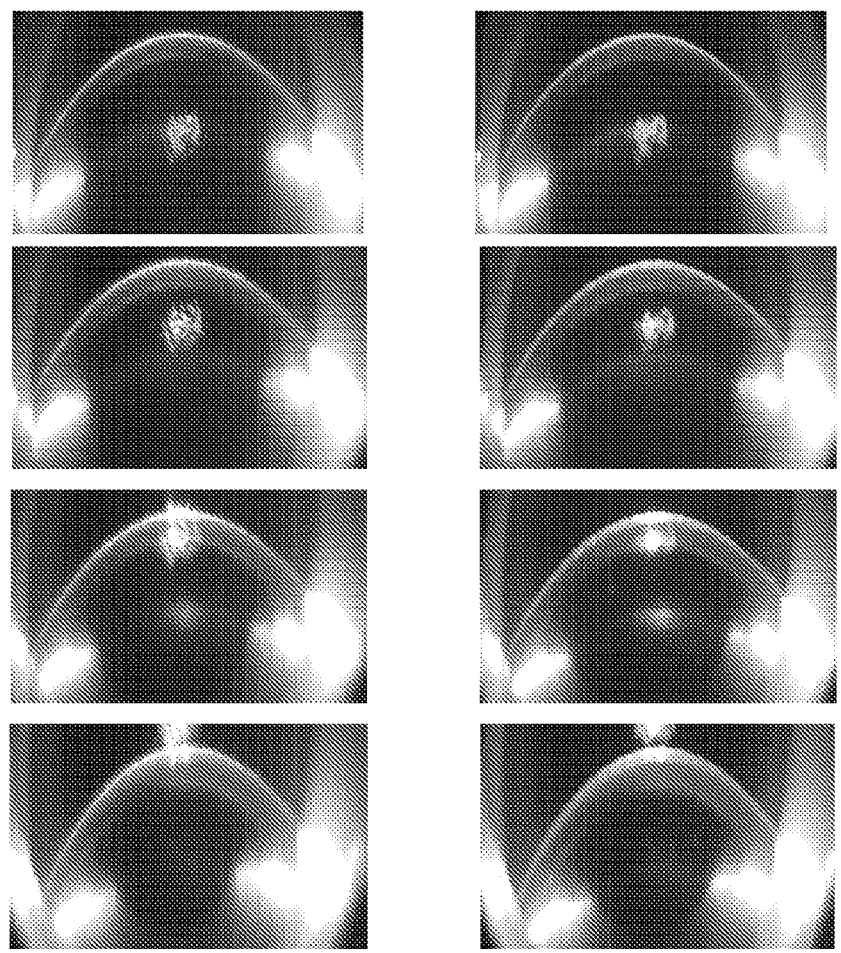
FIG. 10 is a set of Scheimpflug images of a porcine eye in 3D scans with (left) and without (right) the adjustable lens system.

During the 3D scans carried out by the imaging device 100, the incident beam 130 may go beyond the depth of field of the Scheimpflug system 102, which leads to image blurring. By utilizing an adjustable lens 114 or the like, the Scheimpflug system can ensure it can record cross sectional images of the object clearly. FIG. 10 shows the effect of the adjustable lens 114 on the Scheimpflug image.

The use of an electronically-adjustable lens allows the image plane 8 of the Scheimpflug imaging system 102 to intersect the illumination plane of the OCT imaging system 104, without moving the Scheimpflug imaging system 102 camera 112. In this way, both SI and OCT 3D images can be obtained without the need to mechanically rotate the SI and OCT devices. Synchronising the scanning mirror 128 and the adjustable lens allows the illuminated area of the target, for example the eye, to be maintained at the focus plane of the camera of the Scheimpflug imaging system 102. The imaging device may comprise a controller (not shown) to synchronise the beam scanning mechanism and mechanism for providing the adjustable focal length of the Scheimpflug imaging system, such as the adjustable focal length lens, camera mounted on a moveable stage, or the like.

Figure 6A:
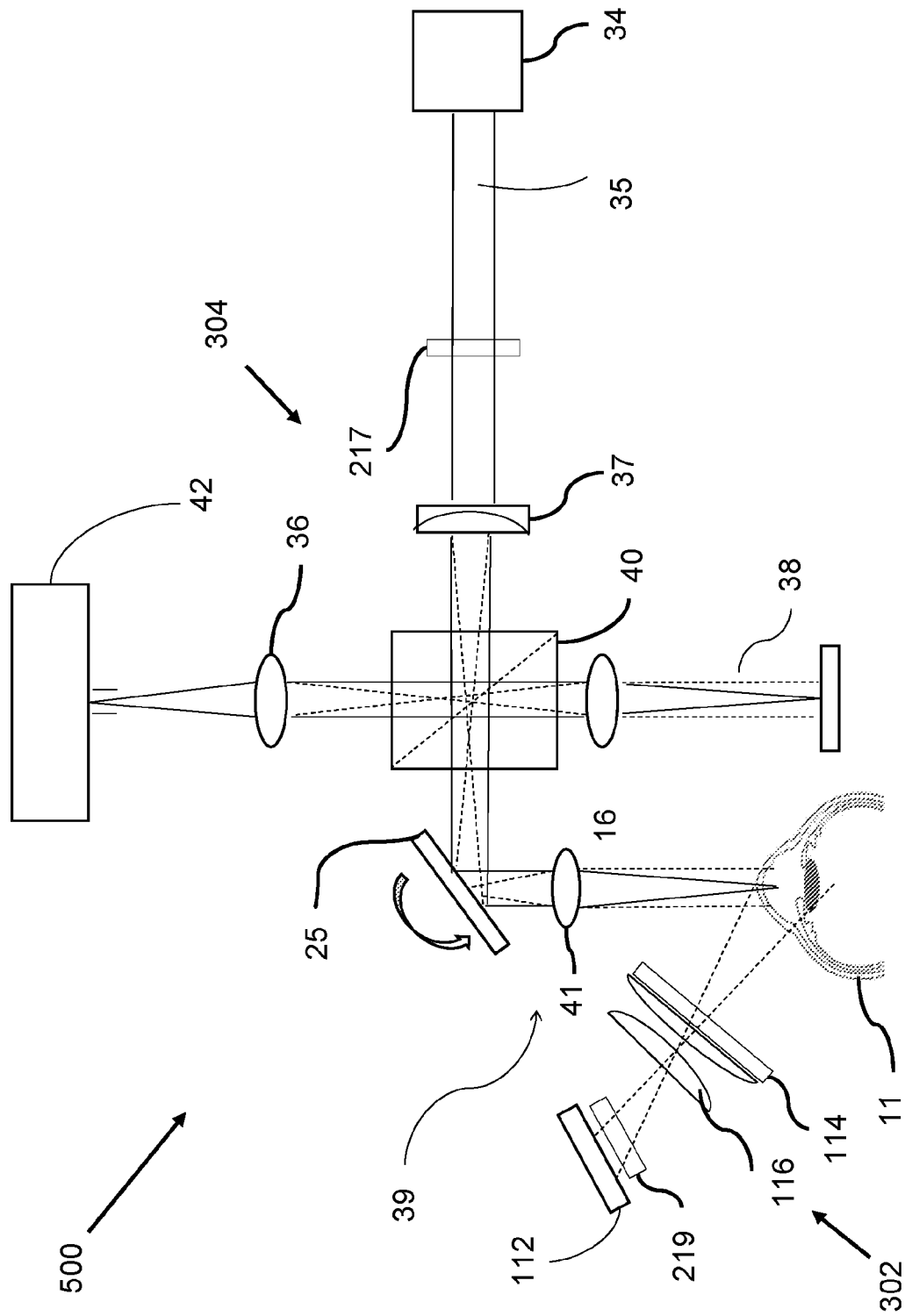
FIG. 6(a) is a schematic illustration of an imaging device according to the disclosure, where the OCT imaging system is in line field configuration.

Referring now to FIGS. 6(a) and (b), there is shown further examples of an imaging device according to the disclosure, indicated generally by the reference numeral 500. The imaging device 500 comprises a line-field spectral domain OCT system indicated generally by the reference numeral 304. The light source 34 emits a beam of parallel near-infrared or visible light 35. Alternatively, the light beam may be generated by placing a point light source at the focal point of a collimation lens (not shown). A cylindrical lens 37 after the polariser 217 focuses the light in one direction. For example, in the vertical direction the light remains parallel but in the horizontal direction it becomes focused. The beam 35 is separated into a reference arm 38 and a sample arm 39 by a beam splitter 40. In FIG. 6(a), an objective lens 41 makes the horizontal direction of the beam 35 focused and the vertical direction parallel at the eye 11, which means that line illumination is performed on both the sample arm 39 and the reference arm 38. Then the returned light from the sample arm 39 and the reference arm 38 passes through a collection lens 36 and is collected by a detector, in this case a spectrometer 42. The main difference compared with a scanning point configuration is that the spectrometer receives full spectral interference signals of an entire B-scan in a single shot in parallel, which largely increases the scanning speed. For the Scheimpflug system, a camera 112 and a lens system 108, including an electrically-adjustable lens 114 and an additional lens 116, are placed according to the Scheimpflug principle.

Figure 6B:
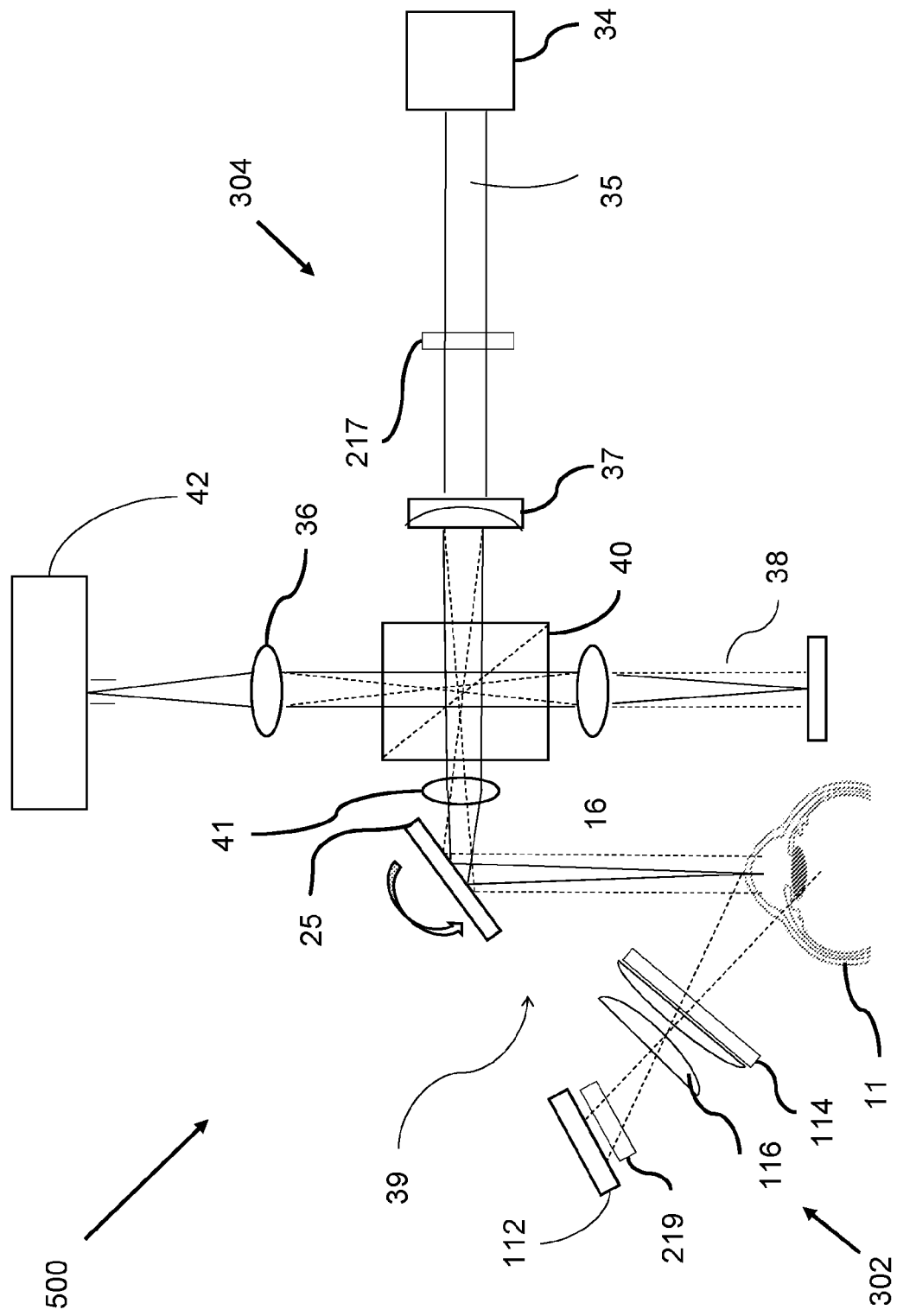
FIG. 6(b) is a schematic illustration of a further imaging device according to the disclosure, where the OCT imaging system is in line field configuration.

The objective lens 41 may be placed either before the Galvanometer scanner 25 (FIG. 6(*a*)) or after the Galvanometer scanner 25 (FIG. 6(*b*)). In FIG. 6(*a*) the electrically-adjustable lens 114 will allow the illuminated target 11 to be maintained at the exact image plane of the SI system whilst in FIG. 6(*b*) the illuminated target will be maintained at the image plane of the SI system within its imaging depth.

One method of constructing an imaging device according to the disclosure would be to construct an OCT imaging system first, either line-field or point scanning OCT, with sufficiently high depth of field of illumination for the following Scheimpflug system. The Scheimpflug imaging system or systems can be constructed adhering to approximate or precise Scheimpflug principles, i.e., the illumination plane, the principal plane of imaging lens and the detection plane intersect at least approximately at the same location. Alternatively the Scheimpflug system could be constructed first, with an appropriate illumination configuration allowing the construction of the OCT imaging system within it.

Figure 7:
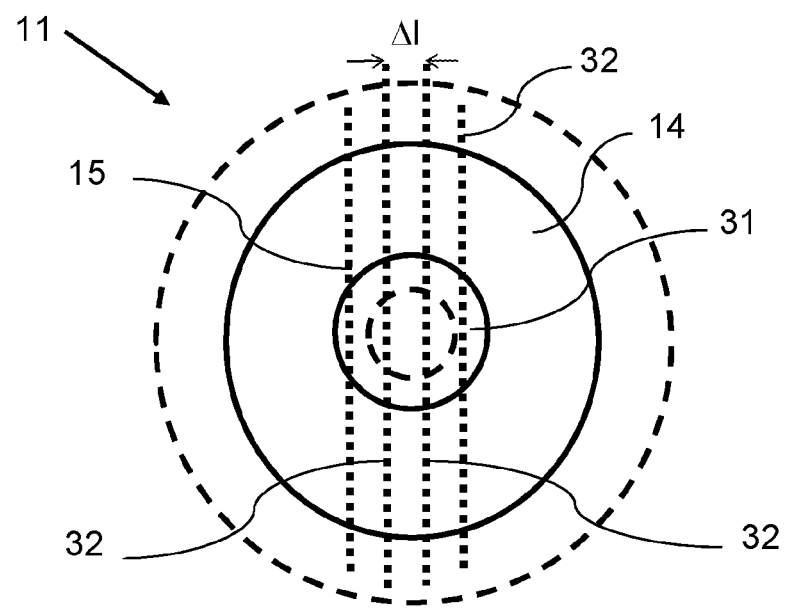
FIG. 7 is a schematic diagram of a front view of an eye in the direction of a visual axis with point scanning illumination.
Figure 8:
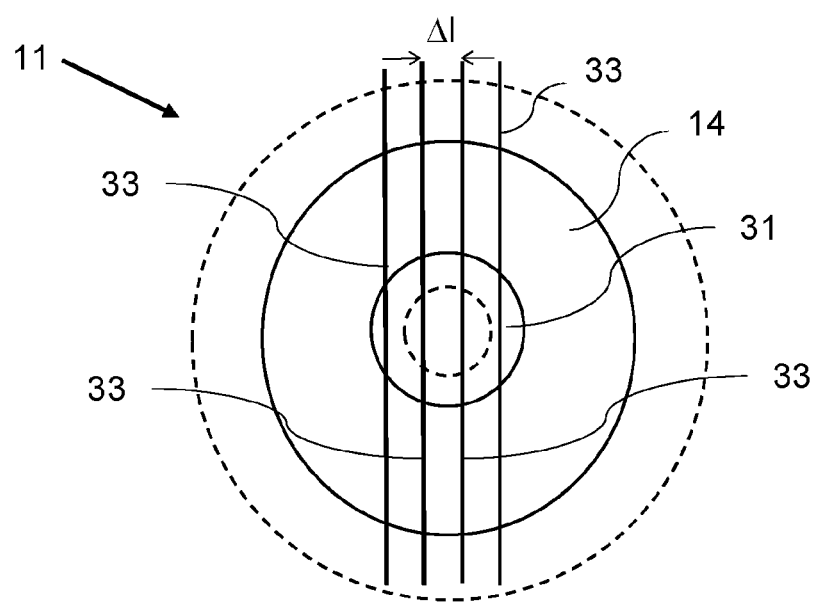
FIG. 8 is a schematic diagram of a front view of an eye in the direction of a visual axis with line field illumination.

FIG. 7 and FIG. 8 each show a schematic diagram front view of the eye 11 having the iris 14 and pupil 31. FIG. 7 further illustrates a plurality of scanning axes 32 corresponding to the scanning point configuration of FIG. 4. FIG. 8 further illustrates a plurality of scanning axes 33 corresponding to the line field configuration of FIGS. 6(*a*) and (*b*). The difference is that each scanning axis 32 under scanning point configuration is formed by many points and each scanning axis 33 under line field configuration is formed by a line. The incident beam 130 carries out the 3D scanning by taking multiple B-scans with Δl adjacent spacing, which follows the scanning axis 32 as the galvanometer scanner 25*a* turns around. Values for Δl may be in the region of 10*s* of micrometers.

Referring now to FIG. 9, there is shown a set of Scheimpflug images of a porcine eye in 3D scans with and without polarizers. The top row of images were captured without polarisers, and the bottom row of images were captured with polarisers. The imaging range of each image is 16 mm×8 mm. From A to E, the incident beam scans five different positions from corneal centre area to side area (scanning range is 4.5 mm) and the camera records cross-sectional images with and without using polarizers. With the scanning, the reflection artefact becomes stronger and covers the useful signal, as can be seen in the top images. This artefact becomes stronger and reaches a maximum at one specific position shown in image pair D group, indicated with a square. The bottom images indicate that the reflection artefact is blocked by polarizers, such that the whole shape of the anterior segment can always be observed.

Referring now to FIG. 10, there is shown a set of Scheimpflug images of a porcine eye in 3D scans with (left) and without (right) the adjustable lens system. The images become blurred when the beam scans from the centre to the peripheral areas because the illuminated area/plane moves outside the image plane of the Scheimpflug camera. When a lens assembly that can provide a variable focal length, such as using an electrically-tuneable lens, is used to bring the illuminated area/plane back to the image plane of the Scheimpflug camera, clear images can be obtained.

Figure 11:
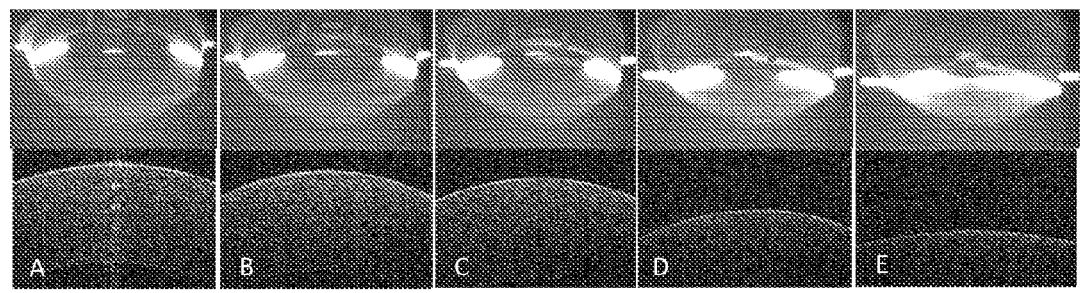
FIG. 11 is a set of Scheimpflug and OCT images of a porcine eye in 3D scans from an imaging device according to the disclosure.

Referring now to FIG. 11, there is shown a set Scheimpflug and OCT images of a porcine eye in 3D scans obtained using an imaging device according to the disclosure. The top row of images are from the Scheimpflug imaging system, and the bottom row of images are from the OCT imaging system using the scanning point configuration. The volumetric data size of the Scheimpflug and OCT are 15 mm×4 mm×13 mm and 4 mm×4 mm×1.4 mm, respectively. From A to E, the beam scans from corneal central area to side area. Each image shows the Scheimpflug image and the OCT image for the same position, which were obtained simultaneously using an imaging device according to the disclosure. The square on the Scheimpflug image indicates the imaging area of the OCT image. The whole shape of the anterior segment of the eye can be observed on the Scheimpflug images (16 mm×13 mm) and the fine structure of the cornea can be visualized on the OCT images (4 mm×1.4 mm).

Figure 12A:
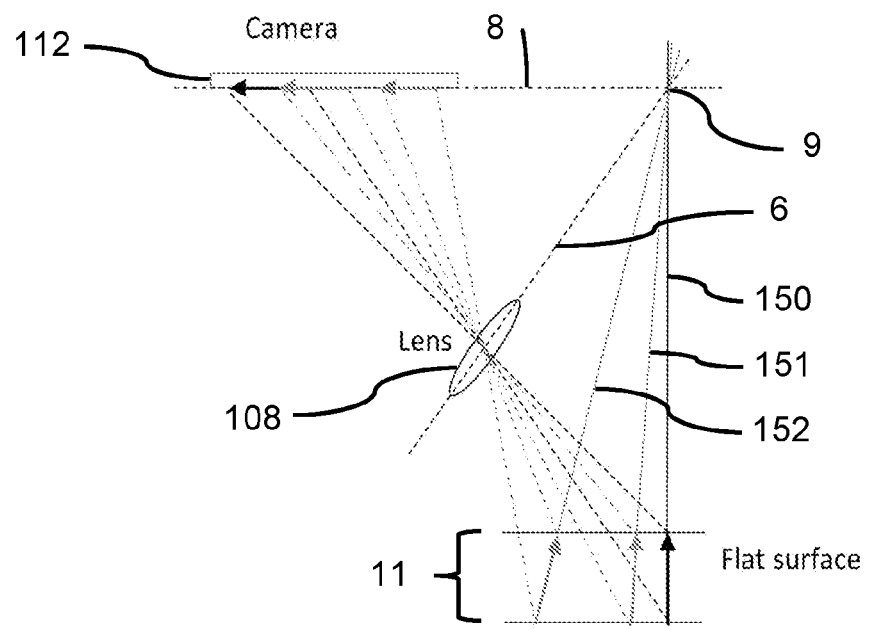
FIG. 12(a) is a schematic diagram of the geometrical relationship in a Scheimpflug Imaging System according to the disclosure, in the case of perfect Scheimpflug arrangement, showing the position change of image planes for a flat surface during 3D scans.
Figure 12B:
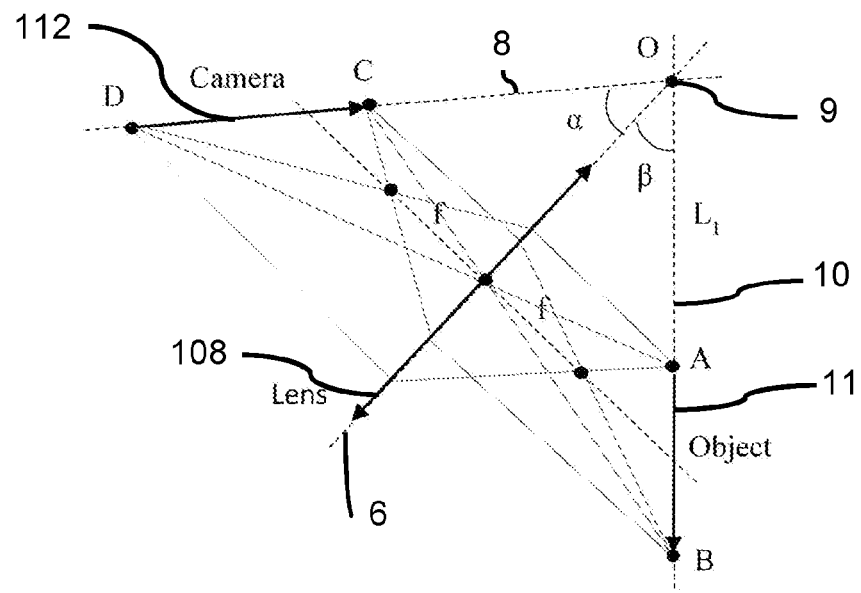
FIG. 12(b) is a schematic diagram of the geometrical relationship in a Scheimpflug Imaging System according to the disclosure, in the case of perfect Scheimpflug arrangement, showing the geometrical relationship of the object and its image plane.
Figure 12C:
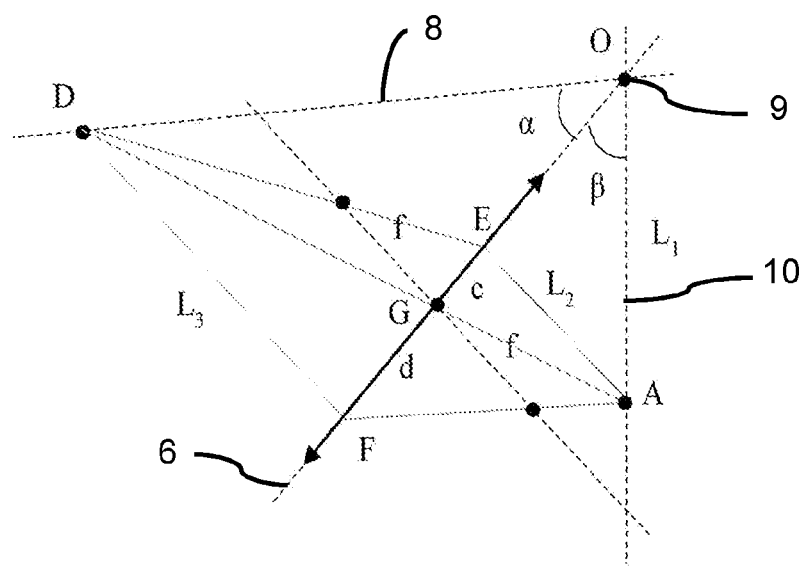
FIG. 12(c) is a schematic diagram of the geometrical relationship in a Scheimpflug Imaging System according to the disclosure, in the case of perfect Scheimpflug arrangement, showing the geometrical relationship of the top of the object and its imaging position.

Referring now to FIG. 12(*a*) there is shown a schematic diagram of the geometrical relationship of the Scheimpflug system showing the position change of image planes for a flat surface during 3D scans. The generation of 3D scans, as described in relation to FIG. 4, comprises obtaining multiple B-scans as the scanning mirror 128 rotates along vertical and horizontal directions sequentially. FIG. 12(*a*) shows the camera 112 having image plane 8, the lens system 108 having principal plane 6, wherein the image plane 8 and principal plane 6 intersect at the Scheimpflug intersection 9. Three positions 150, 151, 152 of a light beam emanating from the intersection 9 are directed at a target 11 having a flat surface and their reflections are focused by the lens system 108 and captured by the camera 112.

As shown in FIG. 12(*a*), during 3D scanning, when the light beam scans across the flat surface of the sample 11, the image on the camera 112 will change as well. Consequently, a sample having a flat surface will appear to have a non-flat surface after 3D image reconstruction of the SI image. The following method may be used to correct this distortion.

A geometrical diagram of the Scheimpflug system is shown in FIG. 12(*b*). The points A and B in the sample plane 10 are recorded as points D and C on the image plane 8, respectively. The following parameters are either known or measurable: $L_1$ is the length between the intersection point 9 (O) and the object A; f is the combined focal length of the adjustable lens system 108; α is the angle between the image plane 8 and the lens plane 6 and β is the angle between the incident beam and the lens plan 6. During 3D scanning, the angle β will change. To facilitate the image reconstruction, the change of the position D is calculated as a function of β.

From FIG. 12(*c*), we have:

$$\frac{f}{L_2} = \frac{d}{c+d} \quad (1)$$

$$\frac{L_2}{L_3} = \frac{c}{d} \quad (2)$$

From equation (1) and (2), equation (3) can be obtained:

$$L_3 = \frac{fL_2}{L_2 - f} \quad (3)$$

And $L_2$ can be expressed by $L_1$:

$$L_2 = L_1 \sin\beta \quad (4)$$

From equation (3) and (4), the length of OD can be expressed as:

$$OD = \frac{L_3}{\sin\alpha} = \frac{fL_1\sin\beta}{(L_1\sin\beta - f)\sin\alpha} \quad (5)$$

Figure 13:
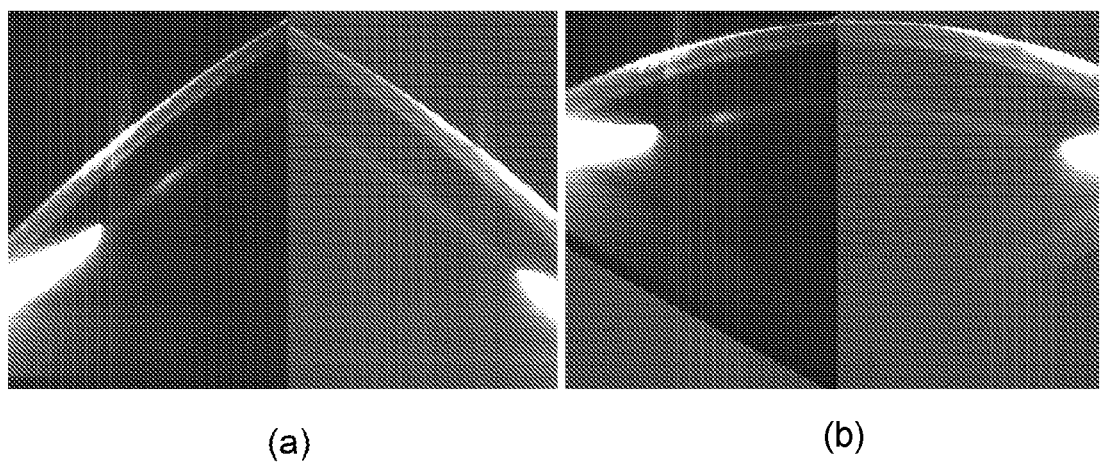
FIGS. 13(a) and (b) show Scheimpflug images of a porcine eye before and after Scheimpflug distortion correction respectively.

FIGS. 13(a) and (b) show the Scheimpflug images of a porcine eye before and after, respectively, the distortion has been corrected using the Equation (5) above. These Scheimpflug images are obtained by jointing two Scheimpflug images captured from two SI systems, for example as shown in FIGS. 7(a) and 7(b). As such, there can be slight differences between the right and the left half parts of the complete image. In FIG. 13(a), the layers of the eye in two sides of the image come together in a point, however, in FIG. 13(b), the layers more closely resemble the curved shape of the cornea. These images demonstrate the reconstruction of the corneal shape after correction of the distortion. The scanning range of these shown images is 9×13 mm².

Figure 14:
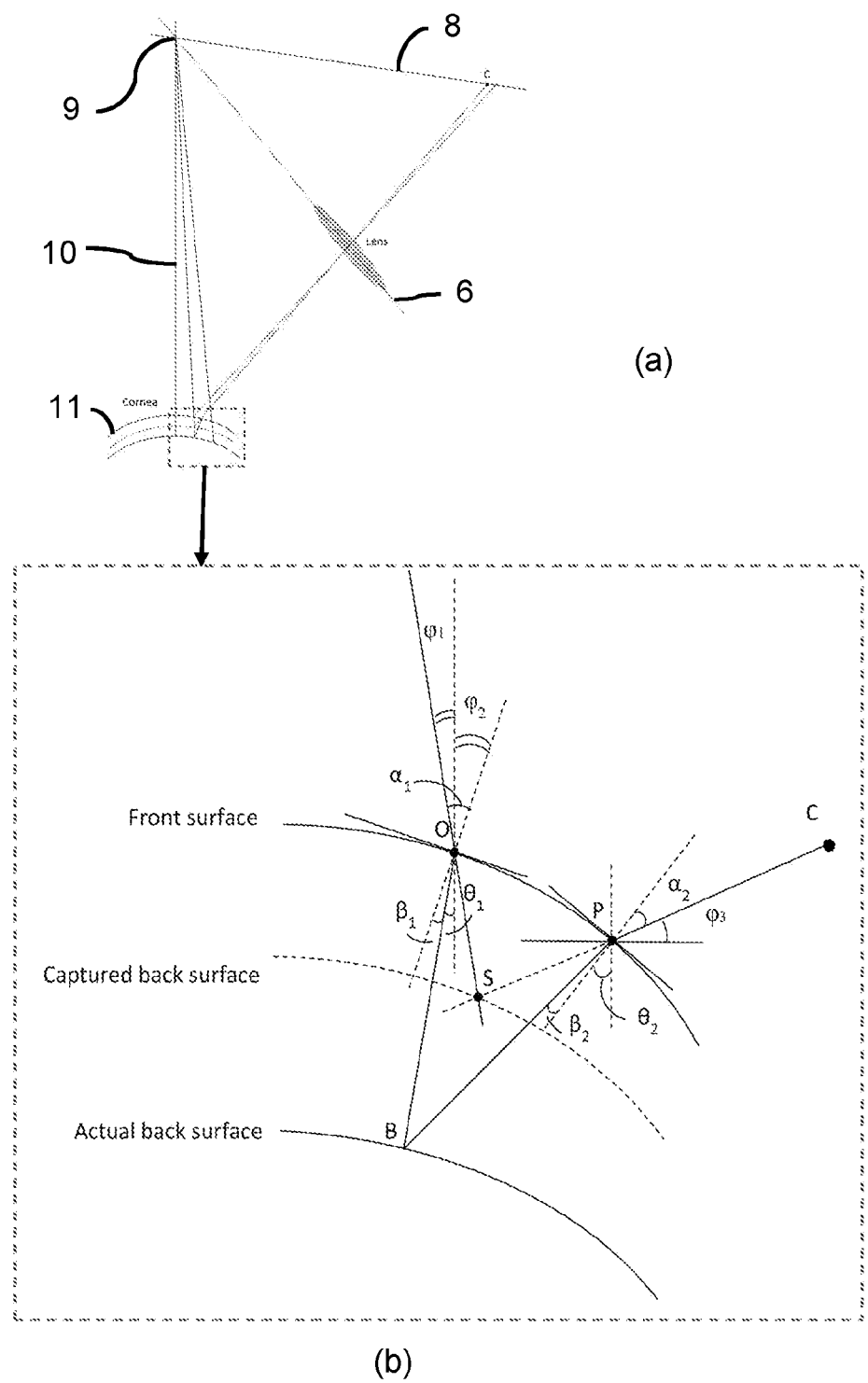
FIG. 14(a) is a schematic diagram of the geometrical relationship of the Scheimpflug system when measuring a cornea.
FIG. 14(b) is a detail view of the portion within the dashed box of FIG. 16(a).

FIGS. 14(a) and 14(b) show the geometrical relationship between the actual illuminating light beam OB and the "visual" light beam OS inside a sample. The following parameters are either known or measurable: the front surface ($y=f_{FS}(x)$), the back surface ($y=f_{BS}(x)$), the incident beam ($y=f_{IB}(x)$), the light incident angle ($\varphi_1$), and camera position point C ($x_C$, $y_C$).

By correcting the refractive effect, it is possible to calculate the actual thickness OB from the "visual thickness OS" of the captured image.

The tangent angle of the front surface at point O ($\varphi_2$) can be obtained by calculating the derivative:

$$\varphi_2 = \frac{\text{diff}(y_o)}{\text{diff}(x_o)} \tag{6}$$

As shown in FIG. 14(b), the incident angle $\alpha_1$ can be calculated:

$$\alpha_1 = \varphi_1 + \varphi_2 \tag{7}$$

The refraction angle $\beta_1$ can be obtained according Snell's law:

$$\frac{\sin\alpha_1}{\sin\beta_1} = n \tag{8}$$

Where n is the refraction index (n=1.376 for cornea). From the definition, the angle $\theta_1$ can be obtained by:

$$\theta_1 = \varphi_2 - \beta_1 \tag{9}$$

The slope of line OB can be calculated:

$$\text{slope}(OB) = \tan(90° - \theta_1) \tag{10}$$

The x and y coordinates of points O and B can be described as:

$$y_B - y_O = (x_B - x_O) \times \text{slope}(OB) \tag{11}$$

As point S is the intersection point of the incident light and back corneal surface, the position of point S ($y_S$, $x_S$) can be obtained by solving the following equations (12) & (13):

$$y_S = f_{IB}(x_S) \tag{12}$$

$$y_S = f_{BS}(x_S) \tag{13}$$

The line SC can be obtained by:

$$\frac{y_C - y_S}{x_C - x_S} = \frac{y_C - y_{SC}}{x_C - x_{SC}} = \text{slope}(SC) \tag{14}$$

The angle $\varphi_3$ can be obtained:

$$\varphi_3 = \arctan(\text{slope}(SC)) \tag{15}$$

As point P is the intersection point of the line SC and front corneal surface, the position of point P ($y_P$, $x_P$) can be obtained by solving the following equations (16) & (17):

$$y_P = f_{FS}(x_P) \tag{16}$$

$$y_C - y_P = (x_C - x_P) \times \text{slope}(SC) \tag{17}$$

Then, the angle $\theta_2$ can be obtained:

$$\theta_2 = \frac{\text{diff}(y_P)}{\text{diff}(x_P)} \tag{18}$$

the angle $\alpha_2$ can be obtained:

$$\alpha_2 = 90° - \theta_2 + \varphi_3 \tag{19}$$

The angle $\beta_2$ can be obtained according Snell's law:

$$\frac{\sin\alpha_2}{\sin\beta_2} = n \tag{20}$$

The slope of line BP can be calculated:

$$\text{slope}(BP) = \tan(90° - \beta_2 - \theta_2) \tag{21}$$

The x and y coordinates of points P and B can be described as:

$$y_B - y_P = (x_B - x_P) \times \text{slope}(BP) \tag{22}$$

Position of point B ($x_B$, $y_B$) can be obtained by getting the solution of equation (11) and (22) because it is the intersection point of the line BP and line BO The actual thickness can be calculated from the corrected positions of front and back surfaces, to the definition required by the user.

By repeating this processing, the actual back surface of the eye can be reconstructed and the actual corneal thickness can be measured.

While the target of the imaging device described herein has been primarily described as an eye, the skilled person will understand that the imaging device may used to image other targets, for example glass, plastics films, transparent objects, translucent objects, ranging and/or topography of any (including opaque and non-transparent) objects.

The Scheimpflug imaging system of the disclosure is configured to maintain the camera at the image plane of the lens system. This may be achieved by way of a lens system which can provide a variation in focal length. While examples using an electrically controlled variable focal length lenses are described herein, the skilled person will understand that other methods of maintaining the camera at the image plane of the lens system are available. For example, a fixed focal length lens (or lens assembly) may be moveable to ensure that a clear image of the eye may be formed at the camera of the SI system. Alternatively, or additionally, the camera may be moveable such that the image plane is maintained thereon. It will be understood that acceptable results are achievable where the image plane is not perfectly positioned on the camera. The variable that is adjusted to maintain the image plane at the camera may be synchronised with the beam scanning mechanism.

Throughout the description and claims of this specification, the words "target" and "sample" may be used interchangeably.

Throughout the disclosure, certain optical elements, such as lenses for light beam-shaping may have been omitted from the figures and their associated description for clarity.

It will be understood that the person skilled in the art would appreciate if and where any such elements would be useful.

Throughout the description and claims of this specification, the OCT imaging system is not limited to being within a strict definition of OCT, but may be understood to include any broadband interferometric reasonably described as OCT. Such devices include spectral domain optical coherence tomography, time domain optical coherence tomography, swept source optical coherence tomography and spectral domain reflectometry.

The controller may comprise a machine-readable medium and a processor. The machine-readable medium may comprise instructions which, when executed by a processor, cause the processor to perform the task described herein actions in line with the methods and examples described herein.

Examples in the present disclosure can be provided as methods, systems or machine-readable instructions, such as any combination of computer programme code, hardware, or the like. Such machine-readable instructions may be included on a machine-readable medium having computer readable program codes therein or thereon. The machine-readable medium can be realised using any type or volatile or non-volatile (non-transitory) storage such as, for example, memory, a ROM, RAM, EEPROM, optical storage and the like. The machine-readable medium may be a non-transitory machine-readable medium. The machine-readable medium may also be referred to as a computer-readable storage medium.

The machine-readable instructions may, for example, be executed by processing circuitry. The processing circuitry may be in the form of or comprised within a computing device. Such a computing device may include a general purpose computer, a special purpose computer, an embedded processor or processors or other programmable data processing devices to realize the functions described in the description and diagrams. In particular, a processor or processing apparatus may execute the machine-readable instructions. Thus, functional modules of the apparatus and devices may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine-readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by flow(s) in the flow charts and/or block(s) in the block diagrams.

Further, some of the teachings herein may be implemented in the form of a computer software product, the computer software product being stored in a storage medium and comprising a plurality of instructions for making a computer device implement the methods recited in the examples of the present disclosure.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An imaging device for imaging a target, comprising:
   a Scheimpflug imaging system having a camera and a lens system configured to provide an adjustable focal length;
   an Optical Coherence Tomography (OCT) imaging system having an imaging optical element and a detector; and
   a light source adapted to provide a light beam suitable for operation of the Scheimpflug imaging system and the OCT imaging system.

2. The imaging device of claim 1, wherein the focal length is adjustable in response to a control signal.

3. The imaging device of claim 1, wherein the lens system comprises a lens having an adjustable focal length.

4. The imaging device of claim 1, wherein the focal length of the lens is electronically adjustable.

5. The imaging device of claim 1, wherein the lens system further comprises an additional lens adapted to provide enhanced focus.

6. The imaging device of claim 2, wherein the OCT imaging system comprises a beam scanning mechanism to control movement of the light beam, and the control signal includes a signal to the beam scanning mechanism to control the beam scanning mechanism in synchronisation with the adjustable focal length.

7. The imaging device of claim 1, wherein the light source comprises a shared single light source adapted to provide illumination to both the Scheimpflug imaging system and the OCT imaging system simultaneously.

8. The imaging device of claim 1, comprising a polarizer arrangement.

9. The imaging device of claim 1, wherein the OCT imaging system is a line-field configuration OCT imaging system.

10. The imaging device of claim 1, wherein the OCT imaging system is a scanning point configuration OCT imaging system.

11. The imaging device of claim 1, wherein the OCT imaging system is a swept source OCT imaging system.

12. The imaging device of claim 1, wherein the OCT imaging system is a spectral-domain OCT imaging system.

13. The imaging device of claim 1, wherein the OCT imaging system is a time-domain OCT imaging system.

14. The imaging device of claim 1, wherein the shared light source is a visible, near infra-red, or infra-red light source.

15. The imaging device of claim 1, wherein the shared light source is a broadband light source.

16. The imaging device of claim 1, comprising two or more Scheimpflug imaging systems.

17. The imaging device of claim 16, wherein each of a pair of Scheimpflug imaging systems are placed on opposite sides of an illumination plane of the imaging device.

18. The imaging device of claim 1, wherein the target is an eye.

\* \* \* \* \*